United States Patent [19]

Kawasaki et al.

[11] Patent Number: 5,154,926
[45] Date of Patent: Oct. 13, 1992

[54] ACETAMINOPHEN OR PHENOBARBITAL SYRUP COMPOSITION

[75] Inventors: Yoshihiko Kawasaki; Yukio Suzuki, both of Tokyo, Japan

[73] Assignee: Showa Yakuhin Kako Co., Ltd., Tokyo, Japan

[21] Appl. No.: 651,298

[22] Filed: Feb. 6, 1991

[30] Foreign Application Priority Data

Feb. 6, 1990 [JP] Japan .................................. 2-26943

[51] Int. Cl.$^5$ ...................... A61K 9/08; A61K 31/05; A61K 31/165; A61K 31/515
[52] U.S. Cl. .................................. 424/439; 514/974; 514/923; 514/849; 514/772.7; 514/774; 514/782
[58] Field of Search ............... 424/439; 514/974, 923, 514/849

[56] References Cited

U.S. PATENT DOCUMENTS

| | | | |
|---|---|---|---|
| 4,684,666 | 8/1987 | Haas | 514/557 |
| 4,816,247 | 3/1989 | Desai et al. | 424/439 |

*Primary Examiner*—Thurman K. Page
*Assistant Examiner*—E. J. Webman
*Attorney, Agent, or Firm*—Oblon, Spivak, McClelland, Maier & Neustadt

[57] ABSTRACT

The present invention relates to a syrup composition characterized in that the composition contains phenobarbital or acetaminophen, a polyhydric alcohol and/or a polymer of a polyhydric alcohol, and a water soluble macromolecule, and the weight ratio of phenobarbital to the polyhydric alcohol and/or the polymer of the polyhydric alcohol is from 1:20 to 1:100, and the weight ratio of phenobarbital to the water soluble macromolecule is from 1:1 to 1:20, which has a reduced bitterness and is easy to take.

23 Claims, No Drawings

ACETAMINOPHEN OR PHENOBARBITAL SYRUP COMPOSITION

BACKGROUND OF THE INVENTION

1. Field of the Invention

The present invention relates to a syrup composition which contains acetaminophen or phenobarbital in a high concentration and has a reduced bitter taste.

2. Description of the Related Art

Acetaminophen and phenobarbital, slightly soluble drugs having a bitter taste, have hitherto been administered in such a state that their bitter taste was masked, namely in the case of an oral solid formulation, as a film coated agent, a microcapsule or the like, and in case of an oral solution, they have been administered after their bitterness was masked by adding a saccharide and/or a perfume to the solution, having them entrapped into inclusion compounds (JPA49-36821) or the like.

However, in the case of oral solid formulations, there has been a defect that it is difficult for young children to take them, and there has further been a problem that since slightly soluble drugs dissolve only in a low concentration, a single dose of the solution becomes too large. Further, as for phenobarbitals, an elixir is being used as an oral solution (Commentary of the Japanese Pharmacopoeia XI, A-57, Jul. 18, 1986 and Documents to be Attached to Drugs for Medical Care, vol. 1, The Pharmaceutical Society, Inc., Tokyo, page 32, 1987). However, since alcohol is contained in the elixir medicament, it is a problem for young children to take the elixir composition.

SUMMARY OF THE INVENTION

Thus, the object of the present invention is to provide a syrup composition which overcomes the above noted disadvantages.

Another object of the present invention is to provide a syrup composition containing acetaminophen or phenobarbital in a high concentration, while having a reduced bitter taste of the drug.

A further object of the present invention is to provide a syrup composition which is easy to take.

Furthermore, another object of the present invention is to provide a syrup composition which can produce a therapeutic effect by means of a small dose.

As a result of various investigations carried out to find a solution to the problem, the present inventors found that when a polyhydric alcohol and/or a polymer of a polyhydric alcohol are/is used as solubilizing agent(s) for acetaminophen and phenobarbital, it is possible to dissolve the slightly soluble drugs in a high concentration, and that by compounding a water soluble macromolecule, it is possible to reduce the bitterness of the polyhydric alcohol and the polymer of the polyhydric alcohol as well as the bitterness of the drugs.

Thus, the present invention provides a syrup composition characterizing in that the composition comprises acetaminophen, a polyhydric alcohol and/or a polymer of a polyhydric alcohol, and a water soluble macromolecule, and the weight ratio of acetaminophen to the polyhydric alcohol and/or the polymer of the polyhydric alcohol is from 1:1 to 1:10, and the weight ratio of acetaminophen to the water soluble macromolecule is from 1:0.1 to 1:2.

Further, the present invention provides a syrup composition characterizing in that the composition comprises phenobarbital, a polyhydric alcohol and/or a polymer of a polyhydric alcohol, and a water soluble macromolecule, and the weight ratio of phenobarbital to the polyhydric alcohol and/or the polymer of the polyhydric alcohol is from 1:20 to 1:100, and the weight ratio of phenobarbital to the water soluble macromolecule is from 1:1 to 1:20.

DETAILED DESCRIPTION OF THE INVENTION

The present invention will be described in detail below.

The polyhydric alcohol to be used in the present invention is an alcohol having two or more hydroxyl groups in a single molecule, and examples of the polyhydric alcohol include dihydric alcohols such as, for example, ethylene glycol and propylene glycol; and trihydric alcohols such as, for example, glycerol.

Among the above polyhydric alcohols, propylene glycol and glycerol are preferred. Further, the polymer of the polyhydric alcohol to be used in the present invention is a compound produced by polymerizing a polyhydric alcohol monomer, and examples of the polymer include polyethylene glycol and polypropylene glycol. Further, it is preferred that the molecular weight of the polymer of polyhydric alcohol is from about 300 to about 400. The polyhydric alcohols or the polymers of polyhydric alcohols may be used alone or in combination. Preferably, a combination of from 1 to 30% by weight of propylene glycol, 20% or less by weight of polyethylene glycol, and 5% or less by weight of glycerol may be used.

Examples of the water soluble macromolecule include polyvinyl pyrrolidone, gum arabic powder, gelatin, and polyvinyl polypyrrolidone, preferably, polyvinyl pyrrolidone. For example, polyvinyl pyrrolidone having a molecular weight of from about 25,000 to about 1,200,000 may preferably used.

The following is an embodiment of the syrup composition of the present invention:

| 100 ml of the syrup composition contains: | |
| --- | --- |
| Acetaminophen | 0.5 to 5 g |
| Glycols | 5 to 30 g |
| Water soluble macromolecule | 0.5 to 5 g |
| Sweet saccharides | 10 to 60 g |
| Purified water | appropriate amount |

Although it is not certain how the syrup composition of the present invention reduces the bitter taste of the drug, it is presumed that a polyhydric alcohol or the polymer of the polyhydric alcohol, added to the composition in order to increase the solubility of the drug up to a high concentration, temporarily changes the fluidity of the membrane of the taste bud cells, and as a result, reduces the bitter taste. Further, it is presumed that the water soluble macromolecule such as, for example, polyvinylpyrrolidone, gum arabic powder and gelatin reduces the irritation caused by propylene glycol and the like.

A reduction of bitterness is observed when acetaminophen, the polyhydric alcohol and/or the polymer of the polyhydric glycol, and the water soluble macromolecule are contained in the syrup composition so that the weight ratio of acetaminophen to the polyhydric alcohol and/or polymer of the polyhydric alcohol is from 1:1 to 1:10 and the weight ratio of acetaminophen to the water soluble macromolecule is from 1:0.1 to 1:2, preferably, the weight ratio of acetaminophen to the polyhydric alcohol and/or a polymer of the polyhydric alcohol is from 1:3 to 1:7 and the weight ratio of acetaminophen to the water soluble macromolecule is from 1:0.1 to 1:1.25. Further, a reduction in bitterness is observed when phenobarbital, the polyhydric alcohol and/or a polymer of the polyhydric alcohol, and the water soluble macromolecule are contained in the syrup so that the weight ratio of phenobarbital to the polyhydric alcohol and/or polymer of the polyhydric alcohol is from 1:20 to 1:100 and the weight ratio of phenobarbital to the water soluble macromolecule is from 1:1 to 1:20, preferably, the weight ratio of phenobarbital to the polyhydric alcohol and/or polymer of the polyhydric alcohol is from 1:40 to 1:60 and the weight ratio of phenobarbital to the water soluble macromolecule is from 1:1 to 1:10. When the compounded amount of the polyhydric alcohol and/or a polymer of the polyhydric alcohol is more than the above amount, there are problems, as regards smell, taste, safety etc., in using said alcohol or said polymer as a pharmaceutical additive, and when the compounded amount is less than the above amount, there is the problem of the crystallization of the drug. Further, when the compounded amount of the water soluble macromolecule is more than the above amount, there is the problem of deposition due to the increase of viscosity, and when the compounded amount is less than the above amount, there is the problem that the bitterness is not reduced. The syrup composition of the present invention may contain sweetening agents such as, for example, sucrose, fructose, D-sorbitol, saccharin sodium, and the mixture thereof. The sweetening agent may generally be used in an amount of from 10 to 60% by weight based on the total weight of the formulation.

Although there is no particular need to adjust the pH of the syrup composition of the present invention, the pH may be adjusted to a stable pH range of the drug according to the properties of the pharmaceutical, as the effective ingredient. For example, it is preferable to adjust the pH to from 3.0 to 8.0 in the case where acetaminophen is used, and it is preferable to adjust the pH to from 3.0 to 7.0 in the case where phenobarbital is used in the composition. In addition, other ingredients may be incorporated in the syrup composition of the present invention, if necessary. Examples of the ingredients include, for example, organic solvents such as alcohols; antiseptics such as, for example, methyl para-hydroxybenzoate, ethyl para-hydroxybenzoate, propyl para-hydroxybenzoate, sodium benzoate, and sorbic acid; perfumes such as, for example, orange essence, lemon essence, and strawberry essence; and dyes authorized to be added to drugs. These ingredient may be added in an amount of about 0.5% by weight based on the weight of the drug.

The syrup composition of the present invention can be prepared, for example, by the process comprising the steps of dissolving the drug in propylene glycol, polyethylene glycol, or the mixture thereof, separately dissolving polyvinylpyrrolidone, saccharin sodium, a saccharide and a perfume in purified water, and mixing these solutions to obtain the syrup composition of the present invention.

The syrup composition of the present invention comprising acetaminophen contains, for example, 1 g or more, preferably from 1 to 4 g of acetaminophen in 100 ml of the composition, and the syrup composition of the present invention comprising phenobarbital contains 0.1 g or more, preferably from 0.2 to 0.5 g of phenobarbital in 100 ml of the composition.

The syrup composition of the present invention comprising acetaminophen is useful for the treatment of fever and pain, and the syrup composition of the present invention comprising phenobarbital is useful for the treatment of insomnia, nervous excitement, convulsion, autonomic seizure and psychomotor seizure.

Usually, a daily dose of from 45 to 60 ml of the syrup composition of the present invention containing acetaminophen is orally administered to an adult patient three times a day.

Likewise, a daily dose of 7 to 50 ml of the syrup composition of the present invention containing phenobarbital is orally administered to an adult patient three times a day. The syrup composition of the present invention is suitable for administration to young children, and in this case the dose may be appropriately increased or decreased depending on the age and condition of the child.

The present invention is specifically described below in the following examples. These examples are intended to be illustrative only and are not intended to limit the scope of the present invention.

EXAMPLE

Example 1

4 g of acetaminophen was added to 5 g of propylene glycol and 16 g of polyethylene glycol 400 (The Japanese Pharmacopoeia) to obtain a solution. Separately, 35 g of sucrose, 0.25 g of saccharin sodium, 1.0 g of polyvinylpyrrolidone K-30 (The Japanese Pharmacopoeia), 0.05 g of propyl para-hydroxybenzoate and orange essence were added to 57 ml of purified water to obtain a solution. These solutions were mixed to obtain the syrup composition of the present invention comprising acetaminophen.

EXAMPLE 2

The syrup composition of the present invention comprising phenobarbital having the following formulation was obtained in accordance with the procedure described in

EXAMPLE 1:

| | |
|---|---|
| Phenobarbital | 0.4 g |
| Propylene glycol | 20.0 g |
| Polyvinylpyrrolidone K-30 | 1.0 g |
| Sucrose | 35.0 g |
| Saccharin sodium | 0.25 g |
| Sodium benzoate | 0.2 g |
| Perfume | trace |
| Purified water | appropriate amount |
| total | 100 ml |

Experiment 1

The following samples containing acetaminophen were prepared as comparative examples and the evaluation of bitterness was carried out thereon using 10 healthy adult volunteers. The results are shown in Table 1.

Comparative Example 1

| | |
|---|---|
| Acetaminophen | 4 g |

-continued

| Propylene glycol | 5 g |
| Polyethylene glycol 400 | 16 g |
| Purified water | appropriate amount |
| total | 100 ml |

Comparative Example 2

| Acetaminophen | 4 g |
| Purified water | appropriate amount |
| total | 100 ml |

Example 3 (present invention)

| Acetaminophen | 4 g |
| Propylene glycol | 5 g |
| Polyethylene glycol 400 | 16 g |
| Polyvinylpyrrolidone K-30 | 1 g |
| Purified water | appropriate amount |
| total | 100 ml |

TABLE 1

| | Degree of bitterness | Number of volunteers |
| --- | --- | --- |
| Comparative Example 1 | Unbearable | 3 |
| | Bearable but bitter | 6 |
| | Not bitter | 1 |
| Comparative Example 2 | Unbearable | 7 |
| | Bearable but bitter | 3 |
| | Not bitter | 0 |
| Example 3 (present invention) | Unbearable | 0 |
| | Bearable but bitter | 2 |
| | Not bitter | 8 |

Experiment 2

The following samples containing phenobarbital were prepared and the evaluation of bitterness was carried out thereon in the same manner as described in Experiment 1. The results are shown in Table 2.

Comparative Example 3

| Phenobarbital | 0.4 g |
| Propylene glycol | 20 g |
| Purified water | appropriate amount |
| total | 100 ml |

Comparative Example 4

| Phenobarbital | 0.4 g |
| Purified water | appropriate amount |
| total | 100 ml |

Example 4 (present invention)

| Phenobarbital | 0.4 g |
| Propylene glycol | 20 g |
| Polyvinyl pyrrolidone K-30 | 1 g |
| Purified water | appropriate amount |
| total | 100 ml |

TABLE 2

| | Degree of bitterness | Number of volunteers |
| --- | --- | --- |
| Comparative Example 3 | Unbearable | 4 |
| | Bearable but bitter | 6 |
| | Not bitter | 0 |
| Comparative Example 4 | Unbearable | 9 |
| | Bearable but bitter | 1 |
| | Not bitter | 0 |
| Example 4 (present invention) | Unbearable | 1 |
| | Bearable but bitter | 2 |
| | Not bitter | 7 |

Experiment 3

Effect of the Amount of the Water Soluble Macromolecule on the Bitterness of the Composition The effective amount of polyvinyl pyrrolidone (PVP) K-30 to reduce the bitterness of the composition was evaluated by using the compositions in which the amounts of the drug and the polyhydric alcohol and/or the polymer of the polyhydric alcohol were held constant. The results are shown in Tables 3 and 4, respectively.

TABLE 3

| 1) Acetaminophen | | PVP (g) | Reduction of bitterness |
| --- | --- | --- | --- |
| Acetaminophen | 4 g | below 0.4 | Ineffective |
| | | 0.5 | Effective (++) |
| Propylene glycol | 5 g | 1.0 | Effective (+++) |
| | | 2.0 | Effective (+++) |
| Polyethylene glycol 400 | 16 g | 4.0 | Effective (+++) |

TABLE 4

| 2) Phenobarbital | | PVP (g) | Reduction of bitterness |
| --- | --- | --- | --- |
| Phenobarbital | 0.4 g | below 0.4 | Ineffective |
| | | 0.5 | Effective (++) |
| Propylene glycol | 20 g | 1.0 | Effective (+++) |
| | | 2.0 | Effective (+++) |

(+) Some reduction of bitterness
(++) Reduction of bitterness
(+++) Extreme reduction of bitterness From the above results, it was observed that the syrup composition of the present invention effectively masks bitterness of the drug and is easy to take.

The syrup composition of the present invention can produce a sufficient therapeutic effect by means of a small amount of administration since it contains a highly concentrated drug, and is very easy to take since the bitterness peculiar to the drug is remarkably reduced, and thus the composition is extremely useful clinically.

We claim:

1. An aqueous oral pharmaceutical composition in the form of a syrup consisting essentially of acetaminophen in an amount of 1 to 4 g in 100 ml of the composition, a polyhydric alcohol and/or a polymer of a polyhydric alcohol, said polymer of a polyhydric alcohol having a molecular weight of 300–400, and a water soluble macromolecule selected from the group consisting of polyvinyl pyrrolidone, gum arabic powder, gelatin and polyvinyl polypyrrolidone, and the weight ratio of acetaminophen to the polyhydric alcohol and/or the polymer of the polyhydric alcohol is from 1:1 to 1:10, and the weight ratio of acetaminophen to the water soluble macromolecule is from 1:0 to 1:2.

2. The syrup composition according to claim 1 where the polyhydric alcohol is selected from the group consisting of ethylene glycol, propylene glycol and glycerol.

3. The syrup composition according to claim 1 where the polymer of the polyhydric alcohol is selected from the group consisting of polyethylene glycol and polypropylene glycol.

4. The syrup composition according to claim 1 where the polyhydric alcohol and the polymer of the polyhydric alcohol is a mixture of from 1% to 30% by weight of propylene glycol, not more than 20% by weight of polyethylene glycol and not more than 5% by weight of glycerol.

5. The syrup composition according to claim 1 where the weight ratio of acetaminophen to the polyhydric alcohol and/or the polymer of raw polyhydric alcohol is from 1:3 to 1:7.

6. The syrup composition according to claim 1 where the weight ratio of acetaminophen to the water soluble macromolecule is from 1:0.1 to 1:1.25.

7. The syrup composition according to claim 1 wherein the composition further comprises 10 to 60% by weight of the composition of a sweetening agent other than said polyhydric alcohol and/or polymer of a polyhydric alcohol.

8. An aqueous oral pharmaceutical composition in the form of a syrup consisting essentially of phenobarbital in an amount of 0.2 to 0.5 g in 100 ml of the composition, a polyhydric alcohol and/or a polymer of a polyhydric alcohol, said polymer of a polyhydric alcohol having a molecular weight of 300–400, and a water soluble macromolecule selected from the group consisting of polyvinyl pyrrolidone, gum arabic powder, gelatin and polyvinyl polypyrrolidone, and the weight ratio of phenobarbital to the polyhydric alcohol and/or the polymer of the polyhydric alcohol is from 1:20 to 1:100, and the weight ratio of phenobarbital to the water soluble macromolecule is from 1:1 to 1:20.

9. The syrup composition according to claim 8 where the polyhydric alcohol is selected from the group consisting of ethylene glycol, propylene glycol and glycerol.

10. The syrup composition according to claim 8 where the polymer of the polyhydric alcohol is selected from the group consisting of polyethylene glycol and polypropylene glycol.

11. The syrup composition according to claim 8 where the polyhydric alcohol and the polymer of the polyhydric alcohol is a mixture of from 1% to 30% by weight of propylene glycol, not more than 20% by weight of polyethylene glycol and not more than 5% by weight of glycerol.

12. The syrup composition according to claim 8 where the weight ratio of phenobarbital to the polyhydric alcohol and/or the polymer of the polyhydric alcohol is from 1:40 to 1:60.

13. The syrup composition according to claim 8 where the weight ratio of phenobarbital to the water soluble macromolecule is from 1:1 to 1:10.

14. The syrup composition according to claim 4 wherein the composition further comprises 10 to 60% by weight of the composition of a sweetening agent other than said polyhydric alcohol and/or polymer of a polyhydric alcohol.

15. A method for reducing fever, comprising orally administering to a mammal an effective amount of an aqueous oral pharmaceutical composition in the form of a syrup consisting essentially of acetaminophen in an amount of 1 to 4 g in 100 ml of the composition, a polyhydric alcohol and/or a polymer of a polyhydric alcohol, said polymer of a polyhydric alcohol having a molecular weight of 300–400, and a water soluble macromolecule selected from the group consisting of polyvinyl pyrrolidone, gum arabic powder, gelatin and polyvinyl polypyrrolidone, and the weight ratio of acetaminophen to the polyhydric alcohol and/or the polymer of the polyhydric alcohol is from 1:1 to 1:10, and the weight ratio of acetaminophen to the water soluble macromolecule is from 1:0.1 to 1:2.

16. The method according to claim 15 where the mammal is a human being.

17. The method according to claim 15 wherein the composition further comprises 10 to 60% by weight of the composition of a sweetening agent other than said polyhydric alcohol and/or polymer of a polyhydric alcohol.

18. A method for reducing pain, comprising orally administering to a mammal an effective amount of an aqueous oral pharmaceutical composition in the form of a syrup consisting essentially of acetaminophen in an amount of 1 to 4 g in 100 ml of the composition, a polyhydric alcohol and/or a polymer of a polyhydric alcohol, said polymer of a polyhydric alcohol having a molecular weight of 300–400, and a water soluble macromolecule selected from the group consisting of polyvinyl pyrrolidone, gum arabic powder, gelatin and polyvinyl polypyrrolidone, and the weight ratio of acetaminophen to the polyhydric alcohol and/or the polymer of the polyhydric alcohol is from 1:1 to 1:10, and the weight ratio of acetaminophen to the water soluble macromolecule is from 1:0.1 to 1:2.

19. The method according to claim 18 where the mammal is a human being.

20. The method according to claim 8 wherein the composition further comprises 10 to 60% by weight of the composition of a sweetening agent other than said polyhydric alcohol and/or polymer of a polyhydric alcohol.

21. A method for the treatment of insomnia, comprising orally administering an effective amount of an aqueous oral pharmaceutical composition in the form of a syrup consisting essentially of phenobarbital in an amount of 0.2 to 0.5 g in 100 ml of the composition, a polyhydric alcohol and/or a polymer of a polyhydric alcohol, said polymer of a polyhydric alcohol having a molecular weight of 300–400, and a water soluble macromolecule selected from the group consisting of polyvinyl pyrrolidone, gum arabic powder, gelatin and polyvinyl polypyrrolidone, and the weight ration of phenobarbital to the polyhydric alcohol and/or the polymer of the polyhydric alcohol is from 1:20 to 1:100, and the weight ratio of phenobarbital to the water soluble macromolecule is from 1:1 to 1:20.

22. The method according to claim 21 where the mammal is a human being.

23. The method according to claim 21 wherein the composition further comprises 10 to 60% by weight of the composition of a sweetening agent other than said polyhydric alcohol and/or polymer of a polyhydric alcohol.

* * * * *